United States Patent
Saito et al.

(10) Patent No.: US 9,245,657 B2
(45) Date of Patent: Jan. 26, 2016

(54) ENERGY MODULATOR

(75) Inventors: Nami Saito, Darmstadt (DE); Christoph Bert, Uttenreuth (DE); Eike Rietzel, Weiterstadt (DE)

(73) Assignee: GSI Helmholtzzentrum Fur Schwerionenforschung GmbH, Darmstadt (DE)

( * ) Notice: Subject to any disclaimer, the term of this patent is extended or adjusted under 35 U.S.C. 154(b) by 0 days.

(21) Appl. No.: 14/236,453

(22) PCT Filed: Aug. 3, 2012

(86) PCT No.: PCT/EP2012/003321
§ 371 (c)(1),
(2), (4) Date: Apr. 3, 2014

(87) PCT Pub. No.: WO2013/017285
PCT Pub. Date: Feb. 7, 2013

(65) Prior Publication Data
US 2015/0123020 A1 May 7, 2015

(30) Foreign Application Priority Data
Aug. 4, 2011 (DE) .......................... 10 2011 109 380

(51) Int. Cl.
*A61N 5/00* (2006.01)
*G21K 1/00* (2006.01)
*A61N 5/10* (2006.01)
*G21K 1/10* (2006.01)

(52) U.S. Cl.
CPC ................ *G21K 1/00* (2013.01); *A61N 5/1043* (2013.01); *A61N 5/1048* (2013.01); *A61N 5/1075* (2013.01); *A61N 2005/1087* (2013.01); *A61N 2005/1095* (2013.01); *G21K 1/10* (2013.01)

(58) Field of Classification Search
CPC ................... A61N 2005/1095; A61N 5/1042; A61N 2005/1096; A61N 5/1067; G21K 1/10
USPC ................................ 250/505.1, 492.1, 492.3
See application file for complete search history.

(56) References Cited

U.S. PATENT DOCUMENTS 5,440,133 A * 8/1995 Moyers et al. ............. 250/492.3
5,668,371 A 9/1997 Deasy et al.
(Continued)

FOREIGN PATENT DOCUMENTS

DE 19907098 A1 8/2000
DE 102007054919 A1 2/2009
(Continued)

OTHER PUBLICATIONS

German Office Action, Serial No. DE 10 2011 109 380.3, Dated: Aug. 4, 2014, Applicant: GSI Helmholtzzentrum fur Schwerionenforschung GmbH u.a.
(Continued)

*Primary Examiner* — Michael Maskell
(74) *Attorney, Agent, or Firm* — Reising Ethington PC

(57) ABSTRACT

The present disclosure relates to a particle energy modulating device for variably changing the energy of the particles of a particle beam. The particle energy modulating device has a variable energy varying device with a control value correcting device for correcting a supplied control value. The control value correcting device corrects the supplied control values through the use of previously determined calibration data.

12 Claims, 4 Drawing Sheets

(56) References Cited

U.S. PATENT DOCUMENTS

Figure 1:
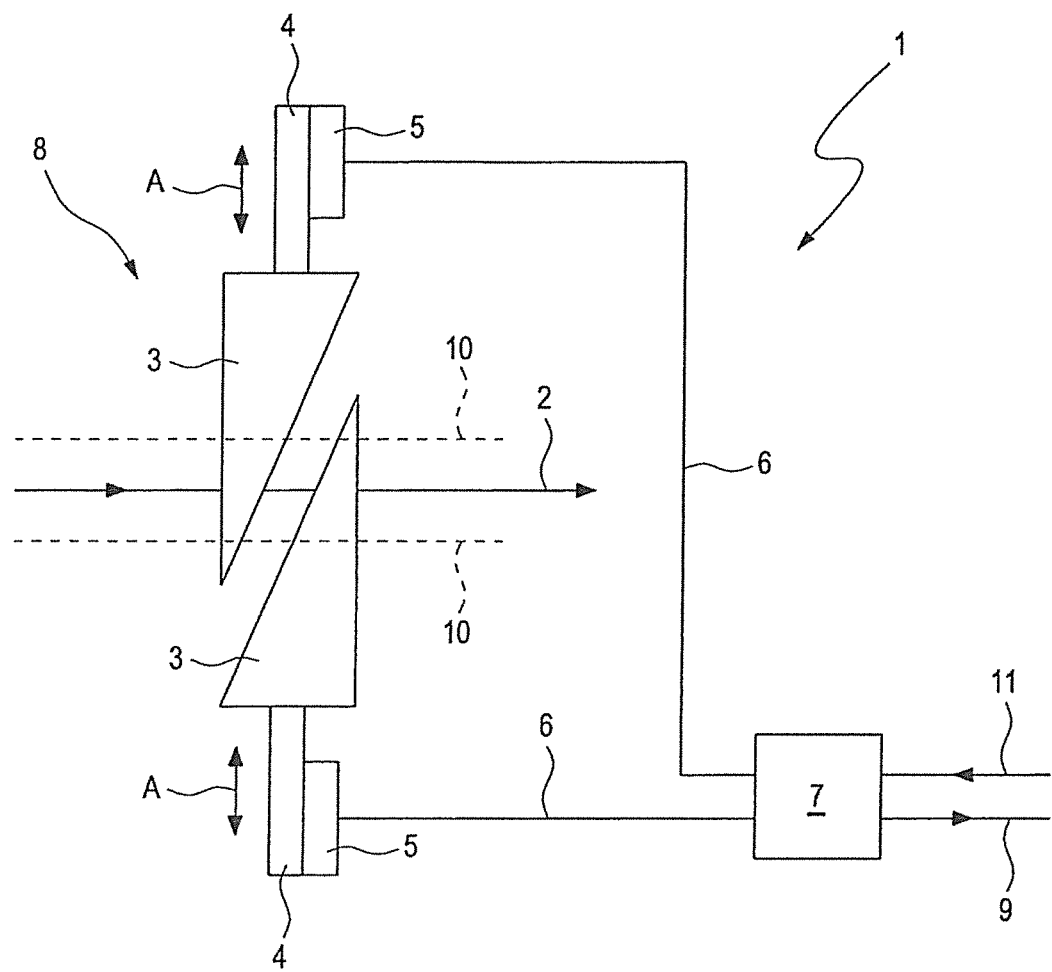

| | | | |
|---|---|---|---|
| 6,891,177 B1 | 5/2005 | Kraft et al. | |
| 2004/0149934 A1 | 8/2004 | Yanagisawa et al. | |
| 2004/0200983 A1* | 10/2004 | Fujimaki et al. | 250/492.3 |
| 2008/0240352 A1 | 10/2008 | Brahme et al. | |
| 2009/0095921 A1* | 4/2009 | Bert et al. | 250/492.1 |
| 2009/0299634 A1 | 12/2009 | Schaffner | |
| 2011/0012028 A1* | 1/2011 | Harada et al. | 250/492.1 |
| 2011/0105821 A1 | 5/2011 | Dieter et al. | |
| 2012/0238795 A1* | 9/2012 | Bert et al. | 600/1 |

FOREIGN PATENT DOCUMENTS

| | | |
|---|---|---|
| EP | 0817210 A1 | 1/1998 |
| EP | 1371390 A1 | 12/2003 |
| JP | 2006034582 A | 2/2006 |

OTHER PUBLICATIONS

Liska, D., Pi-Meson Range Shifter for Clinical Therapy, In:Rev. Sci. Instrum., vol. 48, No. 1, 1977, S. 52-57.

Liska, D. et al., A Clinical Servo System for Shifting the Range of Pion Beams, In: IEEE Trans. on Nuclear Science, vol. NS-24, No. 3, 1977, S. 1046-1048.

Sato, S. et al., A Versatile Control System for Irradiation and Measurement . . . , HIMAC. In: Nuclear Instruments and Methods in Physics Reasearch B, 240, 2005, S.95-99.

Futami, Y. et al., Broad-beam Three-dimensional Irradiation System for Heavy-ion . . . , In: Nuclear Instruments and Methods in Physics Research A, 430, 1999, S. 143-153.

Brusasco, C. et al., A Dosimetry System for Fast Measurement of 3D Depth-dose . . . , In: Nuclear Instruments and Methods in Physics Research B, 168, 2000, S. 578-592.

PCT International Search Report, Int. App. No. PCT/EP2012/003321, Filing Date: Aug. 3, 2012, Date of Mailing Oct. 5, 2012.

DE office Action, Applicant: GSI Gesellschaft fur Schwerionenforschung GmbH, App No. 10 2011 109 380.3, Ref. No. 11GSI0329DEP, Date of Mailing: Apr. 30, 2012.

Eng. Translation of Int. Preliminary Report on Patentability, Int Serial No. PCT/EP2012/003321, Int Filing Date: Aug. 2, 2012, Applicant: GSI Helmholtzzentrum fur Schwerionenforschung GmbH et al, Mail Date: Feb. 2, 2014.

* cited by examiner

ENERGY MODULATOR

BACKGROUND

Meanwhile, articles are subjected to radiation in an extremely wide variety of technical fields. Various types of irradiation methods and different types of radiation are used for this, depending on the requirements for the specific use. Thus, in some technical fields, it is necessary to subject articles to radiation over a large area or in three dimensions and as uniformly as possible in so doing. This is the case, for example, when materials are to be cured or changed in some other way. Meanwhile, it has also become common practice, for example in food technology, to use certain types of radiation in order to extend the shelf life of foods.

In other technical fields, though, subregions of the article to be irradiated must be irradiated with a certain predetermined dosage, typically one that is particularly high. However, the remaining parts of the article normally should either not be irradiated at all or should be irradiated as little as possible. An example of this is the structuring of microprocessors or other microstructures or nanostructures using electromagnetic radiation (sometimes extending into the X-ray range) and image-producing masks.

The dose to be applied into the respective structures can be structured not only in two dimensions, but also in all three spatial directions. A three-dimensional structuring makes it possible, for example, to directly irradiate a volume region contained inside a body to be irradiated without having to open or damage the body (in particular, its outer sheath).

Moreover, the body to be irradiated (or a volume region to be irradiated, which is contained inside the body to be irradiated) is not limited to a static body or an immobile body. Instead, the problem often arises in actual use that the body to be irradiated or parts of the body to be irradiated (e.g., a target volume region to be irradiated) is/are moving. This movement is not limited to an inherently rigid body that is moved relative to an external coordinate system. It is also possible for there to be a relative movement between different regions of the body to be irradiated. This is not necessarily limited to translational movements only. Conceivably, there can also be other types of changes such as rotational movements and changes in density.

In order to be able to irradiate such (sometimes inherently) moving bodies, so-called four-dimensional irradiation methods are used. Ultimately, these are three-dimensional irradiation methods that have a chronological variation (with time functioning as the fourth dimension). Examples of such material irradiation methods can be found in the field of materials sciences, for example in the manufacture of highly integrated components (such as microprocessors and/or memory chips) and in the manufacture of microstructured and nanostructured mechanisms.

Another technical field which has recently begun using three-dimensional or four-dimensional irradiation methods of this kind is in the medical technology sector. Here, too, it is typically necessary to deliver the highest possible dose to certain volume regions inside a body (such as a tumor), while the surrounding (healthy) tissue should either be subjected to the smallest possible dose or preferably not be subjected to essentially any dose at all. This is particularly true when the surrounding tissue constitutes so-called critical tissue such as sensitive organs (referred to in professional circles as an OAR, which stands for "organ at risk"). In this context, this can, for example, be the spinal cord, main blood vessels or neural nodes. Especially when irradiating moving target volumes, a large number of problems arise, some of which have not yet been solved or have not yet been solved to a satisfactory degree.

Essentially, there is a large number of possible solutions. Especially for use with scanning methods, for example, three special approaches will be discussed. These are so-called rescanning methods, gating methods and tracking methods.

In rescanning methods, the body to be irradiated is irradiated in a large number of irradiation scans. With a cyclically repeating movement pattern of the moving body (or of the target area to be irradiated), this therefore results in an irradiation of the target volume that is sufficiently powerful when averaged statistically.

In gating methods, an active irradiation of the target body takes place only when the volume region to be irradiated is in a relatively tightly restricted movement phase. At other times, however, no irradiation occurs.

Especially tracking methods are considered to show particular promise at this time. In tracking methods, the region on which the irradiation finally acts (for example, the zone of the Bragg peak) is moved in accordance with the movement of the volume region of the target body that is to be irradiated.

All three methods have in common the fact that the particle beam (more precisely, the main effective region of the particles) must move (scan) in all three spatial directions. In order to produce a scan in the z direction (the direction essentially parallel to the particle beam), it is thus necessary to vary the energy of the particles.

One possibility for implementing this lies in triggering the particle accelerator itself in a varying fashion so that it emits particles with different energies. The problem with this is that the variation of the particle energy in this case can only occur relatively slowly. In synchrotrons, for example, it has thus far been at best possible to vary the particle energy from one extraction cycle to the next. This results in energy adjustment times in the region of about 10 s. Particularly for tracking methods, adjustment times of this length are too long and are therefore unsuitable. But in rescanning methods and gating methods as well, such long adjustment times result in a significant amount of unnecessary loss in beam time.

The use of passive energy modulators has already been suggested as a possible solution. In these, the particle beam passes through an energy absorbing medium. Through a suitable adjusting mechanism, the medium can be changed in terms of its thickness (as "perceived" by the particle beam) so that the particle beam must travel a different distance through the energy absorbing material. This correspondingly changes the energy of the particles passing through. Examples of such absorber systems include wedge-like or double-wedge-like energy absorber systems. Fast-moving water columns and rotating modulator wheels have also been proposed. Here, too, there is ultimately a change in the distance that the particles must travel through the corresponding modulator material.

Even though such modulator systems are basically suitable for a rapid energy modulation, they still have disadvantages. For example, it has turned out that there can sometimes be considerable discrepancies between a "triggered" energy damping, (i.e. the input value of the control signal) and the actual energy damping by the modulator system. This results in corresponding inaccuracies in the processing method or treatment method, which is correspondingly disadvantageous.

SUMMARY

The object of the present disclosure, therefore, is to propose a particle energy modulating device that is improved relative to the prior art, a control value correcting device that is improved relative to the prior art and a method for determining correction values that is improved relative to the prior art.

The present disclosure attains this object.

The present disclosure relates to a particle energy modulating device for variably changing the energy of the particles of a particle beam passing through the particle energy modulating device, which has at least one variable energy varying device. The present disclosure also relates to a control value correcting device for a particle energy modulating device for variably changing the energy of the particles of a particle beam passing through the particle energy modulating device. The present disclosure also relates to a method for determining correction values, for example, for use for a particle energy modulating device and/or for a control value correcting device of the type described above.

The present disclosure proposes that a particle energy modulating device for variably changing the energy of the particles of a particle beam passing through the particle energy modulating device, which has at least one variable energy varying device, be embodied in such a way that at least one control value correcting device is provided for correcting a control value supplied to a particle energy modulating device; the control value correcting device is embodied and equipped so that the control values supplied to the particle energy modulating device are at least sometimes and/or at least partially corrected through the use of calibration data. The inventors have determined that particle energy modulating devices involve a larger number of potential error sources. For example, material imprecisions can result in a locally different damping effect even though the length of the material through which the beam travels is "suitable." It is likewise possible for production tolerances (particularly in wedge-like absorption systems) to result in unintended thickness fluctuations in the adsorption material. Another potential error source lies in the actuating drives and in the assembly of the particle energy modulating device in the region of the particle beam itself. The multiplicity of potential error sources turns out to be intriguingly systematic in nature. It is thus surprisingly possible to determine suitable calibration data and through the use of these calibration data, to improve the "end result" of the energy modulation of the particles. This can in turn result in an improvement in the quality of the irradiation. Basically, the calibration data can be obtained in any way. It has turned out to be preferable, however, for the calibration data to be arrived at experimentally (i.e., through surveying of the particle energy modulating device). This makes it possible to determine calibration data that are generally particularly exact. Furthermore, such calibration data determined through measurement can be used to correct for a particularly large number of potential error sources. In this context, calibration data should be determined as "late" as possible in the production and assembly process of the particle energy modulating device. For example, the measurement for determining the calibration data may be carried out only after the particle energy modulating device is completed in connection with the particle accelerator device and possibly in connection with the treatment stations and the like (in other words, just before the system is ready to start "production operation"). In the latter case, for example the correction of assembly errors in the assembly of the particle energy modulating device relative to the particle beam guidance (to the beam pipe, etc.) is taken into account.

Another preferred feature is when the correction of control values through the use of calibration data takes place in the particle energy modulating device itself. The particle energy modulating device can then be understood as a "black box," which, when activated with control values, provides a particularly high-quality, precise damping. It is thus possible to use the particle energy modulating device as a "snap-in" solution. It is thus especially easy to carry out, for example, a subsequent installation and/or replacement of a particle energy modulating device. For example, the calculations required for the correction do not necessarily have to be carried out on the computers of the actual accelerator device, thus not necessarily requiring, for example, adjustment of the computing power, changes to the program sequence, or the like.

Basically, the calibration data can be obtained in any way (more precisely stated: they can be obtained at any geometric position). It has turned out to be advantageous, however, if in at least some regions, the calibration data have been determined over an area, such as in the form of a two-dimensional grid. In a multitude of particle energy modulating devices, it is necessary to be able not only to adapt the beam with regard to its energy, but also to change it with regard to its lateral position. For example, the lateral position can normally be changed in two dimensions, i.e., the beam can in principle "sweep across" arbitrary points within a determined area (such as in the iso-energy layer). Together with the modulation of the particle energy (and therefore the position of the iso-energy layer in the z direction), it is thus possible to achieve an inherently arbitrary three-dimensional volume. Naturally, the size and scope of the achievable area and/or achievable volume is limited by the particle accelerator device (including its subsystems, such as the particle energy modulating device, for example). A determination of calibration data over a large area turns out to be advantageous in this case because when, for example, the particle beam is deflected in a lateral direction, particularly significant systematic errors can occur. These can, for example, arise due to the obliquely extending path of the passage, for geometrical reasons, or due to parallax errors. Basically, the determination of calibration data may be carried out in a region such as at the points at which the particle beam strikes the particle energy modulating device—for example, the energy varying device—particularly often.

Including to, but not limited to, when such points do not exist or are not (yet) known, a determination can additionally or alternatively also be carried out in the form of a possibly regular two-dimensional grid. In addition or alternatively to the use of an (otherwise regular) grid, it is also possible for an increased density of measurement points/grid points to be used in the regions in which the particle beam strikes the particle energy modulating device particularly often. In this way, it is possible to take the entire area into account in the correction (even if in only an approximate fashion, depending on the case).

In a particularly preferred modification, the control value correcting device in the particle energy modulating device has at least one interpolation means. With such an interpolation means, it is possible to carry out a (more precise) correction even in regions that do not intrinsically contain a calibration data point (e.g., a measurement value). The intermediate values can, for example, be calculated by means of linear interpolation, cubic interpolation, spline interpolation or other interpolation methods. Naturally, it is also conceivable, in lieu of an interpolation, to also use, for example, the value of the closest adjacent calibration data point.

It has also turned out to be advantageous if the particle energy modulating device, such as the control value correcting device, at least sometimes and/or in at least some areas, carries out a correction with regard to the change in the energy of the particles passing through the particle energy modulating device. As a result, the energy of the particles exiting from the particle energy modulating device can be set to the desired value in a particularly precise way. The proposed correction with regard to the particle energy turns out to be particularly advantageous since normally the particle energy modulating device represents the "last instance" in the modulation of the particle energy to the desired value. Therefore, normally a (new) modulation of the particle energy does not take place, so that the precision of the particle energy modulating device determines the precision of the overall system, at least to a large extent.

It has also turned out to be advantageous if the particle energy modulating device, such as the control value correcting device, at least sometimes and/or in at least some areas, carries out a correction with regard to the trajectory of the particles, such as with regard to their travel direction and/or with regard to a transverse offset thereof. Especially with some designs of particle energy modulating devices (for example, in designs with a wedge-like energy absorber or a double-wedge-like energy absorber), physical effects (in particular diffraction effects) can influence the trajectory of the particles. It is therefore advantageous if this (typically systematic) error is likewise taken into account. The taking into account of this error can be comprised in that its existence triggers an (additional) correction of the particle energy. The correction, however, can also be comprised in that for example, the effects on the particle trajectory are reduced or (essentially) prevented.

In another embodiment of the particle energy modulating device, the particle energy modulating device, such as the control value correcting device, has at least one preferably electronic computing device and/or at least one preferably electronic memory device. For example, numerical/digital systems can be used as the electronic computing device and/or as the electronic memory device. These can include not only conventional computing devices, but for example also single-board computers and the like. For example, these can be embodied in the form of stand-alone units. It is also possible, however, to execute the functionality quasi-simultaneously, for example on a multitasking-capable computing device (which is already provided in any case). With the aid of a computing device, it is possible to carry out the correction (such as interpolations) in a particularly flexible manner. In the memory device, it is possible to store, for example, the determined calibration data. The memory device can be embodied in any form, for example in the form of memory chips, but can also be embodied in the form of a hard disk drive or the like. Preferably, it is (at least partially) comprised of a nonvolatile memory so that the data are not lost, even in the event of a power outage.

It is also advantageous if the particle energy modulating device, preferably the at least one variable energy varying device, has at least one energy absorption device which is at least partially and/or in at least some areas embodied, for example, as a sliding-wedge device, as a fast-moving water column device and/or as a modulator wheel device. Although it is basically possible for the particle energy modulation to occur not only through a "braking" of the particles but also through an "acceleration" thereof, it has turned out to be much simpler if preferably, or only, a braking of the particles occurs in the particle energy modulating device. In actual practice, this is much easier to manage and/or achieve. An output energy increase as needed eventually from time to time can be achieved in that the energy of the particles exiting the particle accelerator is suitably increased in order to then be reduced again in the particle energy modulating device to the precise, respectively desired value. The particle accelerator output energy can be increased, for example, on the particle accelerator side (after an increase of its particle energy, the particle accelerator side correspondingly adapts the control value signal transmitted to the particle energy modulating device). In addition or alternatively, however, it is also possible for the particle energy modulating device to transmit a corresponding feedback signal to the particle accelerator device when it is not able (any longer) to produce the respective currently desired value. Incidentally, this can relate not only to the increase of the particle accelerator output energy, but also logically to a reduction of the particle accelerator output energy. For example, sliding-wedge devices, fast-moving water column devices, and/or modulator wheel devices have proven to be preferred embodiments for the energy absorption device. This is particularly true for sliding-wedge devices. Sliding-wedge devices can be embodied not only as individual sliding wedges, but also (preferably) as double-wedge systems. It is also possible to provide a large (preferably even) number of wedges. Providing an even number of wedges is particularly advantageous because for geometrical reasons, this makes it possible on the "hardware side" to minimize errors that can arise due to a lateral deflection of the particle beam. As a rule, this advantage balances out the disadvantage that arises due to the usually more complex design and overcompensates for it.

The present disclosure also proposes a control value correcting device for a particle energy modulating device for variably changing the energy of particles of a particle beam passing through the particle energy modulating device, in which the control value correcting device is embodied and equipped so that the control values supplied to the control value correcting device are at least sometimes and/or at least partially corrected through the use of calibration data. It is possible in this case to embody and/or modify the control value correcting device in accordance with the above description. For example, a control value correcting device of this kind is especially advantageous for use in one of the above-described particle energy modulating devices. With a corresponding embodiment and/or modification of the control value correcting device, it also has the above-described advantages in an analogous fashion.

The present disclosure also proposes a method for determining correction values, such as to be used for a particle energy modulating device, for a control value correcting device of a particle energy modulating device or for a control value correcting device with the above-described design in which at least one calibration value, preferably a plurality of calibration data points, is determined. The determination can—as has already been basically described above—be carried out both mathematically and based on measurements. The use of measurements is preferable in this case. It is also preferable for the measurements to be carried out as "late" as possible so that the largest possible number of (systematic) error sources can be taken into account in the calibration values.

The proposed method can be embodied—or, as the case may be, modified—in accordance with the above description. In analogous fashion, the proposed method then has the advantages and properties already described above.

For example, it is possible to modify the method so that the calibration data are determined for an arrangement extending over an area, or, as the case may be, for a grid arrangement extending over an area. The particular advantages and properties that can be achieved by means of this have already been (at least basically) described above.

Another particularly preferred modification of the method is comprised in that the data are acquired before a use of the control value correcting device and/or before a use of the particle energy modulating device and/or are stored in a preferably electronic memory device. As has already been explained above, the data should be acquired as "late" as possible so that the largest possible number of potential error sources can be taken into account. Otherwise, please refer (at least basically) to the above description of possible embodiments, possible modifications, advantages, and properties.

DESCRIPTION OF DRAWING FIGURES

Figure 2:
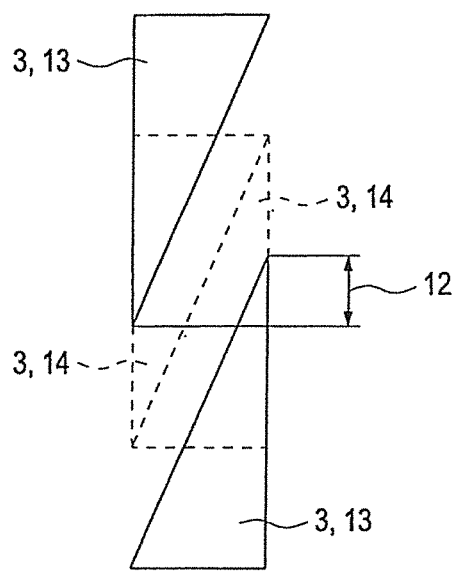
Figure 3:
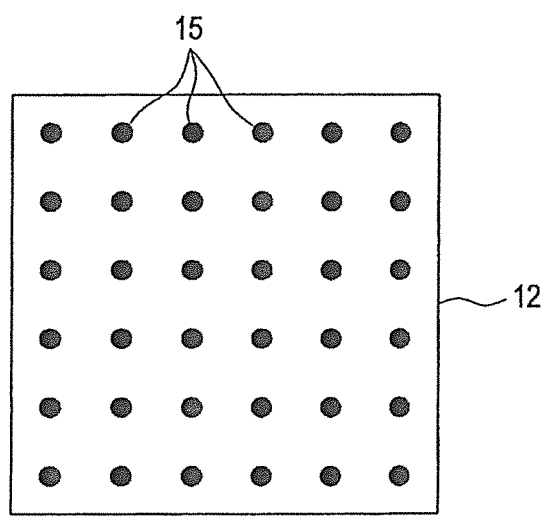
Figure 4:
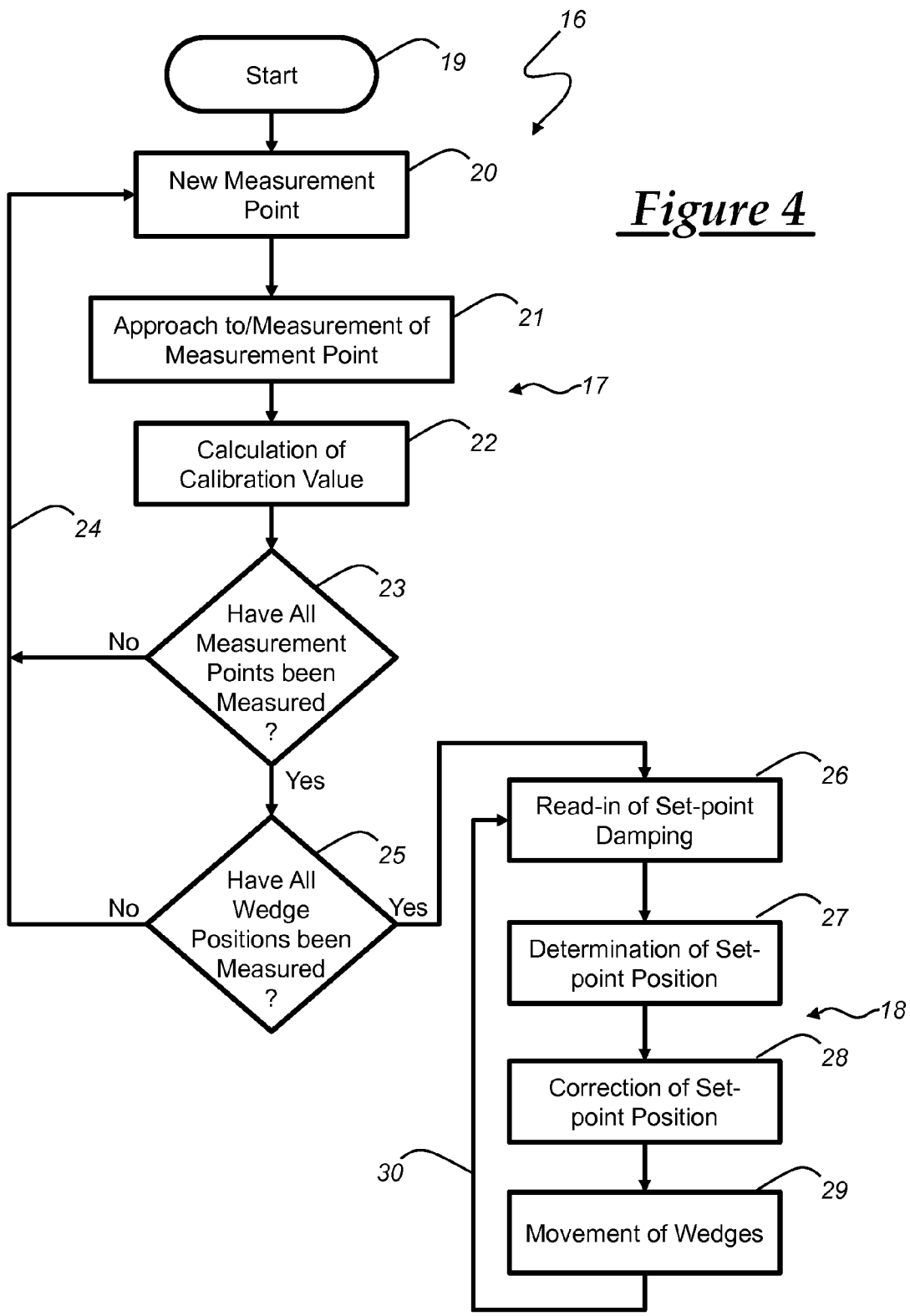

The present disclosure will be described in greater detail below in conjunction with illustrative embodiments and with reference to the accompanying drawings. The drawings show:

FIG. 1: a schematic depiction of a double-wedge energy absorber for a particle beam;

FIG. 2: a schematic top view of the different maximum positions of the energy modulator shown in FIG. 1;

FIG. 3: a schematic depiction of a measurement point grid for determining calibration data;

FIG. 4: a schematic flowchart of a particle energy modulating method.

DETAILED DESCRIPTION

FIG. 1 is a schematic perspective depiction of an energy modulator 1 with its essential subassemblies. The energy modulator 1 is used for varying intensity damping (energy absorption; deceleration) of a particle beam 2 passing through the energy modulator 1. The actual damping of the particle beam 2 takes place in the—in this case—two wedges 3 that are arranged so that they are centrosymmetrical to each other. The two wedges 3 are made of an energy absorbing material having a high material homogeneity. In actual practice, however, material inhomogeneities and/or inhomogeneities in the surface (form inhomogeneities) inevitably occur in the production of the wedges 3. As a result, (initially) erratic fluctuations occur in the damping of the particle beam 2 passing through the energy modulator 1. A typical material for the wedges 3 is Plexiglas. Basically, however, it is also possible to use other materials for this purpose.

The two wedges 3 are each fastened to retaining rods 4 and can be moved relative to each other by means of linear motors 5 (each indicated by a respective double arrow A in FIG. 1). The linear motors 5 are activated via control cables 6 by an electronic computer 7, which in this instance, is embodied in the form of a single-board computer. The activation in this case is carried out in such a way that the two wedges 3 are moved in the same way as and in opposite directions from each other, either toward or away from each other. Depending on the position of the two wedges 3 relative to each other, the particle beam 2 (as is clearly visible in FIG. 1) travels a different distance through the material of the two wedges. Since the energy damping correlates to the distance traveled inside the material of the wedges 3, the particle beam 2 undergoes a different intensity of damping between its entry into the energy modulator 1 and its exit from the energy modulator 1. The subassembly composed of the two wedges 3 therefore functions purely as an energy damping unit 8 whose damping action, however, can be changed with the aid of linear motors 5. An acceleration of the particle beam 2 is not possible with the structural design of the energy modulator 1 shown here. If it should be necessary to increase the energy beyond the maximum possible initial value of the energy modulator 1 (minimum damping action of the energy damping unit 8), then the electronic computer 7 can send a signal via a data line 9 to the particle accelerator (not shown) connected upstream of the energy modulator 1 so that this particle accelerator increases the particle energy by a suitable amount. The same can also apply if the desired particle energy must be lowered to a level that lies below the minimum initial energy of the energy modulator 1 (maximum damping action of the energy damping unit 8).

Because of the symmetrical design and arrangement of the wedges 3, the damping action of the double-wedge system (of the energy damping unit 8) does not change if the particle beam 2 makes a laterally offset entry into the energy modulator 1 (two laterally offset particle beams 10 are depicted in FIG. 1). This is due to the fact that with the laterally offset particle beam 10, the distance that the laterally offset particle beam 10 travels for example in the front wedge 3 accounts for a correspondingly decreased distance in the rear wedge 3 (and vice versa). Naturally, it is not possible here to prevent the fact that higher-order effects can result in a (usually smaller) change in the damping action of the particle beam 2, 10.

The energy modulator 1 is activated via a data line 11 that leads into the electronic computer 7. (Uncorrected) control values such as a desired damping action of the energy damping unit 8 can be input via the data line 11. These control values can, for example, be predetermined by a central computer of the particle accelerator that produces the particle beam 2, 10. The input via the data line 11, however, is not necessarily limited to this. For example, additional information such as the magnitude of a lateral offset of a laterally offset particle beam 10 can also be sent via the data line 11. With such data, it is possible for the electronic computer 7 to carry out a better correction of the damping action of the energy damping unit 8 (described below). The input data about the lateral offset do not necessarily have to be measurement values, but can, for example, also be the control values that are sent to a unit that causes the lateral offset of the particle beam 2, 10. For such a lateral offset unit, it is possible, for example, to use two pairs of magnetic coils (not shown here) that are situated at right angles to each other (and are each perpendicular to the direction of the particle beam). Merely for the sake of completeness, it should be noted that the data line 11 can, for example, be embodied in the form of a packet-oriented data line (for example, Ethernet protocol, token ring protocol, fiber-optic data cable, etc.). Particularly with such a "packet-oriented" design, it is also possible to have the data line 11 for the input signal and the data line 9 for the feedback signal embodied in the form of a combined data line (not shown here).

In FIG. 2, the two wedges 3 of the energy modulator 1 shown in FIG. 1 are respectively shown in a position 13 in which they are spaced the maximum distance apart from each other and in a position 14 in which they are spaced the minimum distance apart from each other (depicted with dashed lines). The usable region 12 for the damping of the particle beam 2, 10 is defined in this case by the overlapping region of the two wedges in the position 13 in which they are spaced the maximum distance apart from each other. This usable region 12 is depicted in a top view in FIG. 3.

In FIG. 3, a plurality of measurement points 15 is shown inside the usable region 12. In the exemplary embodiment shown here, the measurement points 15 are arranged in the form of a regular grid. The distance between two measurement points 15 in the present case is respectively constant both along a row and along a column. However, other patterns are basically also possible. For example, a cluster of points can be established in a region that is typically or more frequently struck by the particle beam 2, 10.

The individual measurement points 15 are approached one after another (also see FIG. 4), for example, after installation of the energy modulator 1 into the particle accelerator device. The actual damping action for each of the individual measurement points 15 is experimentally determined through measurement. The difference between actual and "theoretical" damping is individually calculated for each measurement point 15 and stored in a memory unit of the electronic computer 7 (for example in the form of a so-called "look-up" table). These values are then used as calibration data in a "production operation" of the particle accelerator or energy modulator 1.

The measurement of the actual damping per measurement point 15 in this case is carried out not only in a single position of the two wedges 3 relative to each other, but also both at the maximum distance 13 and minimum distance 14 of the two wedges 3 from each other and also at a suitably large number of intermediate positions.

The density of the point grid 15 and the number of the intermediate positions of the two wedges 3 relative to each other should, on the one hand, be chosen to be large enough to permit a sufficiently good calibration, but, on the other hand, should also be chosen to be small enough so that the measurement does not take an inordinate amount of time. If, during "production operation," a value is requested that has not been measured, then it is possible, for example, to use the value of the closest adjacent measurement point 15. It is also possible, however, to determine a value by using interpolation methods on the adjacent measurement points 15.

FIG. 4 depicts the method 16 that can be used for "designing" and operating an energy modulator (for example the energy modulator 1 shown in FIG. 1). The overall method 16 is essentially composed of two submethods 17, 18, namely, the method for determining calibration data 17 and the method for correcting control values 18. In this case, it is possible for the method 17 to be carried out, for example, only one single time and for the calibration data determined in this case to be stored in a nonvolatile memory of an electronic computer 7. It is, however, also possible for the method for determining calibration data 17 to be carried out at periodic intervals. For example, it is possible for the method for determining calibration data 17 to be carried out at the start of each therapy day, for example, in order to have respectively up-to-date correction data on hand.

The overall method 16 starts with the starting step 19. In this step, for example, the electronic computer 7 is initialized and the like.

In a first method step 20, a first (or a new) measurement point 15 is determined, which must be approached in order to measure the actual damping action of the energy damping unit 8 and/or of the energy modulator 1. The new measurement point 15 determined in 20 is then approached in 21. A corresponding signal can be output, for example, via the feedback data line 9. In addition, the actual damping action is measured in method step 21.

As soon as the results are produced, the data acquired in step 21 are used to calculate 22 the valid calibration value for the current measurement point 15.

This completes the measurement of the first measurement point 15. Then, in a checking step 23, a check is run as to whether all of the measurement points 15 of the measurement grid have already been measured. If this is not the case, then the method returns 24 to step 20 in which a new measurement point 15 is determined. If, however, the grid has been completely measured, then in a subsequent checking step 25, a check is run as to whether all of the desired positions of the wedges 3 relative to one another have been measured. If this is not the case, then the two wedges 3 are moved into a new position relative to each other and the method returns 24 to method step 20 in which a new (first) measurement point 15 is determined 20, which is then measured.

On the other hand, if all wedge positions have been measured, then the method for determining calibration data 17 is finished, and the method for determining corrected control values 18 is begun. In this method, a desired damping value that is to be taken into account by the energy damping device 8 and/or the energy modulator 1 is read-in 26 via a data line 11. The data are provided, for example, by the main computer of a particle accelerator system. Based on this setpoint value, in a subsequent step 27, the setpoint position of the wedges 3 relative to each other is determined in a "zero$^{th}$ approximation." This can, for example, be carried out using analytical methods.

The setpoint values thus determined are corrected in a subsequent method step 28. This uses the calibration data acquired in the first method block 17. Through the correction of the control values, it is possible to take into account, for example, inhomogeneities with regard to the surface of the wedges 3, with regard to the material of the wedges 3 (e.g. different material densities), with regard to control value errors of linear motors 5 and the like. The correction of the control values 28 can achieve an increased precision of the actual damping action of the energy modulator 1 and/or energy damping unit 8.

In a subsequent method step 29, the corrected position setpoint values thus acquired are implemented, i.e., the wedges 3 are moved 29 into the corresponding, corrected setpoint position. Then, the method returns 30 to the method step 26 in which a new setpoint value is read-in.

The invention claimed is:

1. A particle energy modulating device for variably changing the energy of particles of a particle beam passing through the particle energy modulating device, which has at least one variable energy varying device, characterized by at least one control value correcting device for correcting a control value supplied to the particle energy modulating device; the control value correcting device is embodied and equipped so that the control values supplied to the particle energy modulating device are at least sometimes and/or at least partially corrected through the use of calibration data characterized in that in at least some regions, calibration data have been determined over an area in the form of a two-dimensional grid including a plurality of measurement points where actual damping action is measured for calculating values of the calibration data.

2. The particle energy modulating device according to claim 1, characterized in that the control value correcting device has at least one interpolation means.

3. The particle energy modulating device according to claim 1, characterized in that the control value correcting device, at least sometimes and/or in at least some areas, carries out a correction with regard to the change in the energy of the particles passing through the particle energy modulating device.

4. The particle energy modulating device according to claim 1, characterized in that the control value correcting device, at least sometimes and/or in at least some areas, carries out a correction with regard to the trajectory of the particles.

5. The particle energy modulating device according to claim 1, characterized in that the control value correcting device has at least one electronic computing device and/or at least one electronic memory device.

6. The particle energy modulating device according to claim 1, characterized in that the at least one variable energy varying device has at least one energy absorption device, which is at least partially and/or in at least some areas embodied as a sliding-wedge device, as a fast-moving water column device, and/or as a modulator wheel device.

7. A control value correcting device for correcting a control value supplied to a particle energy modulating device for variably changing the energy of the particles of a particle beam passing through the particle energy modulating device, characterized in that the control value correcting device is embodied and equipped so that control value supplied to the particle energy modulating device are at least sometimes and/or at least partially corrected through the use of calibration data, characterized in that in at least some regions, calibration data have been determined over an area in the form of a two-dimensional grid including a plurality of measurement points where actual damping action is measured for calculating values of the calibration data.

8. A method for determining correction values for a particle energy modulating device, wherein the method comprises:
   determining calibration data over a grid arrangement extending over an area, including:
     approaching a measurement point,
     measuring actual damping action of an energy damping unit and/or an energy modulator at the measurement point, and
     calculating a valid calibration value for the current measurement point; and
   determining corrected control values, including:
     reading in a desired damping value for the energy damping device and/or the energy modulator,
     determining a setpoint position of at least one energy absorption device,
     correcting the determined setpoint position using the valid calibration value to result in a corrected setpoint position, and
     adjusting the at least one energy absorption device into the corrected setpoint position.

9. The method according to claim 8, characterized in that the calibration data are acquired before a use of the control value correcting device and/or before a use of the particle energy modulating device and/or are stored in an electronic memory device.

10. The particle energy modulating device according to claim 4, wherein the correction is carried out with regard to a travel direction of the particles and/or with regard to a transverse offset of the travel direction.

11. The method according to claim 8, characterized in that the step of determining corrected control values, at least sometimes and/or in at least some areas, includes carrying out a correction with regard to the change in the energy of the particles passing through the particle energy modulating device.

12. The method according to claim 8, characterized in that the step of determining corrected control values, at least sometimes and/or in at least some areas, includes carrying out a correction with regard to the trajectory of the particles.

* * * * *